United States Patent [19]

Betzold

[11] Patent Number: 5,123,412
[45] Date of Patent: Jun. 23, 1992

[54] DUAL-CHAMBER PACEMAKER WITH AUTOMATIC SELECTION OF ATRIAL REFRACTORY PERIOD

[75] Inventor: Robert A. Betzold, Fridley, Minn.
[73] Assignee: Medtronic, Inc., Minneapolis, Minn.
[21] Appl. No.: 567,432
[22] Filed: Aug. 14, 1990
[51] Int. Cl.⁵ ........................................... A61N 1/368
[52] U.S. Cl. ............................................... 128/419 PG
[58] Field of Search ................................. 128/419 PG

[56] References Cited

U.S. PATENT DOCUMENTS

| | | | |
|---|---|---|---|
| 3,648,707 | 3/1972 | Greatbatch | 128/419 P |
| 4,059,116 | 11/1977 | Adams | 128/419 PG |
| 4,344,437 | 8/1982 | Markowitz | 128/419 PG |
| 4,363,325 | 12/1982 | Koline et al. | 128/419 PG |
| 4,401,119 | 8/1983 | Herpers | 128/419 PG |
| 4,407,287 | 10/1983 | Herpers | 128/419 PG |
| 4,412,541 | 11/1983 | Schaldach et al. | 128/419 PG |
| 4,421,116 | 12/1983 | Markowitz | 128/419 PG |
| 4,428,378 | 1/1984 | Anderson et al. | 128/419 PG |
| 4,467,807 | 8/1984 | Bornzin | 128/419 PG |
| 4,515,161 | 5/1985 | Wittkampf et al. | 128/419 PG |
| 4,539,991 | 9/1985 | Boute et al. | 128/419 PG |
| 4,554,921 | 11/1985 | Boute et al. | 128/419 PG |
| 4,712,556 | 12/1987 | Baker, Jr. | 128/419 PG |
| 4,714,079 | 12/1987 | Hedberg et al. | 128/419 PG |
| 4,781,194 | 11/1988 | Elmqvist | 128/419 PG |
| 4,825,870 | 5/1989 | Mann et al. | 128/419 PG |
| 4,856,523 | 8/1989 | Sholder et al. | 128/419 PG |
| 4,890,617 | 1/1990 | Markowitz et al. | 128/419 PG |
| 4,920,965 | 5/1990 | Funke et al. | 128/419 PG |

OTHER PUBLICATIONS

Rate Responsive Dual Chamber Pacing.

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

An improved atrial synchronous dual-chamber pacemaker provided with a variable refractory period during which the pacemaker is not responsive to sensed atrial contractions. The atrial refractory period is selected based upon whether the ventricular pacing pulse preceding the refractory occurred as a result of time out of the interval corresponding to the basic ventricular pacing rate, or due to time out of the A-V delay interval initiated in response to sensing of a natural atrial contraction. The pacemaker may most easily be practiced by modifying a DDD type pacemaker, and employing the V-A interval, normally separating an atrial pacing pulse from an immediately preceding ventricular contraction, as an extended atrial refractory period, employed only after generation of a ventricular pacing pulse not triggered by a preceding atrial contraction.

6 Claims, 5 Drawing Sheets

DUAL-CHAMBER PACEMAKER WITH AUTOMATIC SELECTION OF ATRIAL REFRACTORY PERIOD

BACKGROUND OF THE INVENTION

This invention pertains generally to the field of electrical heart pacemakers and more specifically to pacemakers of the type in which pacing rate is regulated by means of a sensor responsive to the patient's need for cardiac output and to pacemakers adapted to operate in an atrial synchronous mode, generally referred to as "VDD" pacemakers.

VDD pacemakers are first disclosed in U.S. Pat. No. 3,648,707 issued to Wilson Greatbatch on Mar. 14, 1972. This pacemaker included electrodes for sensing contractions of the atrium and ventricle and a pulse generator for pacing the ventricle. After sensing a contraction of the ventricle or pacing the ventricle, a lower rate timer was restarted. If this timer expired, it triggered generation of a ventricular pacing pulse. Also included was an A-V interval timer, initiated in response to the sensing of an atrial contraction. On expiration of this timer, the ventricular pacing pulse would also be triggered. The pacemaker included a third timer, defining an upper rate interval initiated following ventricular pacing or sensing of a ventricular contraction. During the upper rate interval, time out of the A-V interval would not be effective to trigger a ventricular pacing pulse. This allowed for inhibition of the ventricular pulse generator in the event that a natural ventricular contraction followed a sensed atrial contraction. It also defined a maximum synchronous pacing rate, corresponding to the upper rate interval. If the atrial rate exceeded this rate, the pacing rate would fall to the higher of one-half of the sensed atrial rate or the rate determined by the lower rate timer.

An improvement to this pacemaker was set forth in U.S. Pat. No. 4,059,116 issued to Adams on Jan. 12, 1976, incorporated herein by reference in its entirety. In this pacemaker, rather than preventing generation of a ventricular stimulus in response to time out of the A-V interval during the upper rate interval, the stimulus was instead delayed until the expiration of the upper rate interval. In addition, a post-ventricular atrial refractory period was defined after each ventricular pacing pulse and each sensed ventricular contraction, during which an atrial contraction would not initiate timing of the A-V interval. The net result of these features was to produce a pacemaker which displayed an improved response to atrial contractions occurring at intervals less than the upper rate interval. The pacemaker in this case generated ventricular stimulation pulses separated by the upper rate interval, displaying gradually lengthening A-V intervals until an atrial contraction fell within the post-ventricular atrial refractory period. The pacemaker would resynchronize on the next subsequent atrial contraction, mimicking the natural condition known as Wenckebach behavior. In commercially marketed pacemakers employing the Adams invention, the behavior of the pacemaker in the presence of high natural atrial rates is referred to as "Pseudo-Wenckebach" upper rate behavior.

Recently, variation of pacing rate in response to sensed physiologic parameters, such as physical activity, oxygen saturation, blood pressure and respiration has been the subject of much research and development activity. U.S. Pat. No. 4,428,378 issued to Anderson et al discloses a pacemaker which varies its pacing rate in response to sensed physical activity. Pacemakers as described in this patent have been widely commercialized. A similar pacemaker, varying its pacing rate in response to variations in oxygen saturation, is disclosed in U.S. Pat. No. 4,467,807, issued to Bornzin.

Physiologic sensors have been integrated into dual chamber pacemakers, as illustrated in U.S. Pat. No. 4,890,617, issued to Markowitz et al on Jan. 2, 1990, incorporated herein by reference in its entirety. In this patent, a DDD type pacemaker having pacing intervals regulated by a sensor responsive to physical activity is disclosed. In this device, a fixed post-ventricular atrial refractory period is defined following each ventricular pacing pulse.

An additional dual chamber rate responsive pacemaker is disclosed in U.S. Pat. application Ser. No. 07/249,046 filed Sept. 23, 1988, by Barouh Berkovits for a "DUAL CHAMBER RATE RESPONSIVE PACEMAKER", also incorporated herein by reference in its entirety. In this pacemaker, atrial rate is monitored and, in response to an atrial rate in excess of a predetermined upper rate operation of the pacemaker is changed to desynchronize it from the atrium, with pacing rate controlled by a sensor of the patient's demand for cardiac output. This pacemaker also employed a fixed post-ventricular atrial refractory period.

An additional dual chamber, rate responsive pacemaker is described in the article entitled "Rate Responsive Dual Chamber Pacing", published in *Pace*, Vol. 9, Nov.–Dec. 1986, pp. 987–991. In this device, regulation of the pacing rate was determinable either by the natural atrial rate or the activity rate. The pacemaker was so configured that it would not follow atrial rates substantially in excess of the rate defined by the sensor. This was accomplished by extending the post-ventricular atrial refractory period in response to detection of an atrial rate substantially in excess of the sensor determined pacing rate.

Numerous patents have dealt with dual chamber pacemakers which vary their post-ventricular atrial refractory periods in an attempt to prevent generation of pacemaker mediated tachycardias (PMT's). One such pacemaker is disclosed in U.S. Pat. No. 4,920,965 issued May 1, 1990 for a "DUAL CHAMBER PACEMAKER WITH ADAPTIVE ATRIAL ESCAPE INTERVAL", incorporated herein by reference in its entirety. In this pacemaker, a post-ventricular atrial refractory interval is calculated based upon the time of occurrence of the atrial contraction, relative to the preceding ventricular pacing pulse or sensed ventricular contraction. This pacemaker gradually decreased its post-ventricular atrial refractory period in response to increasing natural atrial rates. Alternatively, it has been suggested to monitor the timing of atrial contractions with respect to previous ventricular contractions and if their timing indicates that the atrial contractions are probably retrograde P-waves, to extend the post-ventricular atrial refectory period beyond the measured time of occurrence of the retrograde P-waves. Such pacemakers are disclosed in U.S. Pat. Nos. 4,544,921 and 4,503,857, issued to Boute et al.

SUMMARY OF THE INVENTION

The present invention is embodied in a VDD pacemaker of the type generally described in the above cited Greatbatch and Adams patents. The pacemaker may also employ a sensor of physiologic demand for cardiac output, as in the above cited Markowitz et al patent or in the above cited Berkovits application. As in the pacemakers described in these patents and applications, ventricular pacing pulses are generated either as a result of time-out of an A-V delay interval, initiated on sensing of atrial contractions or as a result of time-out of a lower rate timer, defining a maximum interval between ventricular pacing pulses. Unlike the pacemakers described in the cited patents and applications, a pacemaker according to the present invention defines different post ventricular atrial refractory periods depending upon whether the ventricular pacing pulse was triggered as a result of the expiration of the A-V interval, or as a result of expiration of the lower rate interval. Pacing pulses triggered due to expiration of the A-V interval are followed by a relatively short, fixed atrial refractory period, typically less than 400 ms. and preferably about 250 ms. This refractory period allows the pacemaker to follow physiologically-appropriate high atrial rates. Following pacing pulses generated by time-out of the lower rate interval, a second, substantially longer postventricular atrial refractory period is provided. This lengthened refractory period extends from the pacing pulse to a predetermined period before the next scheduled lower rate ventricular pacing pulse. This lengthened postventricular atrial refractory period prevents against the pacemaker generating closely spaced ventricular pacing pulses either as a result of retrograde conduction or as a result of occurrence of a bradycardic atrial contraction in close proximity to a ventricular pacing pulse.

In those cases in which the pacemaker takes the form of a rate-responsive pacemaker, the refractory period following time-out of the rate responsive lower rate interval will vary, expiring a predetermined time prior to the next scheduled ventricular pacing pulse. As the rate responsive lower rate interval decreases as a result of the sensor indicating an increase in demand for cardiac output, the postventricular atrial refractory period simultaneously decreases. This allows for continued synchronization with appropriately timed atrial contractions, even at high ventricular pacing rates.

The present invention is particularly convenient to implement, in that it can be incorporated by means of relatively minor changes in circuitry to preexisting DDD or DDDR type pacemakers, preferably those which have the ability to provide a longer A-V interval following an atrial pacing pulse than following a sensed atrial contraction. In such pacemakers, the present invention may be practiced by disabling the atrial output circuit, and by making minor circuitry changes, employing timing signals already present in the pacemaker to define a modified atrial refractory period following ventricular pacing pulses generated at the expiration of the lower rate interval.

DETAILED DESCRIPTION OF THE PREFERRED EMBODIMENTS

The present invention is believed employable in the context of any VDD, VDDR, DDD or DDDR type dual-chamber pacemaker. However, as discussed above, the particular embodiment illustrated is particularly adapted to be employed in a DDD or DDDR type pacemaker of the type capable of defining different A-V delays following atrial pacing pulses and sensed atrial contractions. In the embodiment illustrated, timing functions are performed by digital circuitry, with the refractory period decoded by means of digital logic gates. However, the present invention might also be employed in a microprocessor-based pacemaker in which timing and logic operations take place under software control, rather than being hardwired into the pacemaker circuitry. Alternatively, the invention might also be accomplished using analog timing circuitry as in the above cited Adams and Greatbatch patents.

Figure 1:
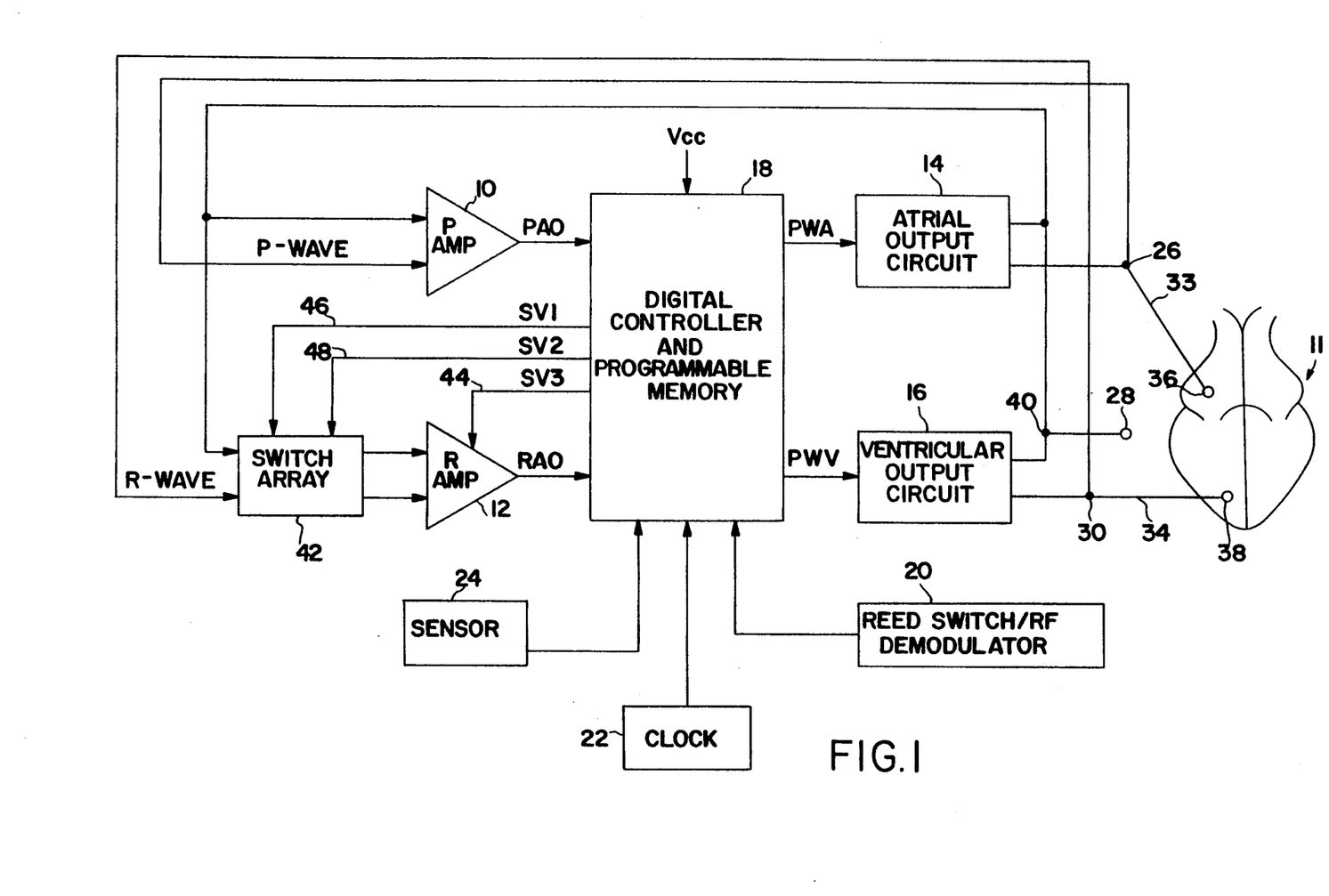
FIG. 1 is a block functional diagram of a DDD type pacemaker in which the present invention may be practiced.

The basic functional structure of the pacemaker is illustrated in FIG. 1. Its operation can best be understood in conjunction with the simulated EKGs and timing charts illustrated in FIGS. 2 and 3.

FIG. 1 shows a general, functional diagram of a DDD type pacemaker. The general functional organization illustrated is known to the art, and serves as the backdrop for the present invention. The pacemaker is coupled to the heart 11 by means of atrial electrode 36, ventricular electrode 38 and indifferent electrode 28. Natural contractions of the atrium are sensed between electrode 28 and electrode 36. Natural contractions of the ventricle are sensed between electrode 28 and electrode 38. As illustrated, electrode 36 is located on a cardiac pacing lead 33, and is coupled to the atrium of the heart 11. Ventricular electrode 38 is located on a second pacing lead 34, and is coupled to the ventricle of the heart. Electrode 28 may be the metallic housing of the pacemaker. Alternatively, bipolar electrode pairs in the atrium or ventricle may also be used.

Signals indicative of natural atrial contractions are sensed between electrodes 28 and 36 by P-wave amplifier 10, which generates output signals indicative of the detection of natural atrial contractions. Electrical signals indicative of ventricular contractions are sensed between electrode 28 and 38 by R-wave amplifier 12, which generates output signals indicative of ventricular contractions. Electrodes 28 and 38 are coupled to R-wave amplifier 12 via switch array 42 which serves to disconnect R-wave amplifier 12 from electrodes 28 and 38 during delivery of atrial pacing pulses. Digital controller 18 provides signals on lines 46 and 48 which controls switch array 42, preventing signals being applied to R-wave amplifier 12 during generation of atrial and ventricular pacing pulses. The operation of R-wave amplifier is controlled by timing signals on line 44. The operation of R-wave amplifier is controlled by timing signals on line 44. Sensor 24 is an optional feature, and responds to the patient's physiologic demand for oxygenated blood as in the above-cited U.S. Pat. No. 4,890,617.

In its preferred embodiments, a pacemaker according to the present invention will be controllable by means of an RF link between an external programmer and the implanted pacemaker. Adjustment of the parameters of digital controller 18 is accomplished by means of reed switch/RF demodulator 20, which functions generally as disclosed in U.S. Pat. No. 4,420,120, issued to Hartlaub et al., also incorporated herein by reference in its entirety. Any programming/telemetry system according to prior art may be used to perform this function. Crystal clock 22 provides timing signals to digital controller 18.

Under control of digital controller 18, atrial output circuit 14 provides stimulating pulses to the atrium of the heart 11 via electrodes 36 and 28. Under control of digital controller 18, ventricular output circuit 16 similarly applies stimulating pulses to the ventricle of the heart 11 by means of electrodes 28 and 38. Timing and control of stimulating pulses provided by atrial output circuit 14 and ventricular output circuit 16 is described in more detail in the timing charts illustrated in FIGS. 2 and 3. All timing intervals illustrated in FIGS. 2 and 3 are controlled by digital controller 18, and with the exceptions noted below correspond generally to the operation of prior art DDD type pacemakers.

In the present invention, atrial output circuit 14 is presumed to be disabled. A common method of accomplishing this function in prior art pacemakers is to program the atrial output circuit to an output of zero, via the programming/telemetry system. Prior art pacemakers also are typically programmable as to pacing mode, with programming options typically including the ability to program the device into one of a number of atrial synchronous modes, such as DDD, VDD or VAT pacing. The present invention is intended to become operative when the pacemaker is programmed to disable the atrial output circuit 14, and is programmed to an atrial synchronous pacing mode. In other operative modes, it is envisioned that the pacemaker will function similarly to DDD type pacemakers.

Figure 2:
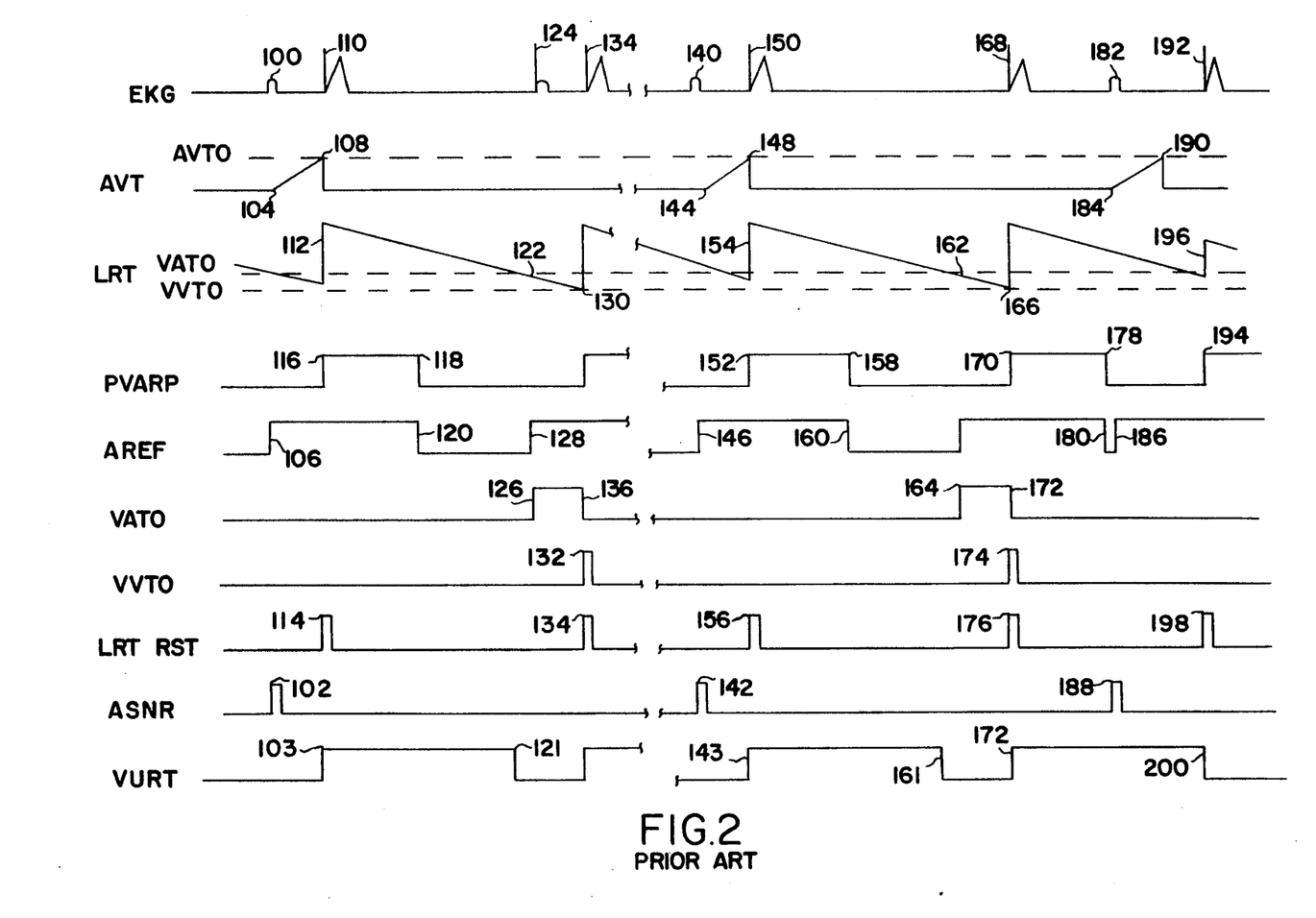
FIG. 2 illustrates the operation of the pacemaker in FIG. 1, with atrial pacing disabled.
Figure 3:
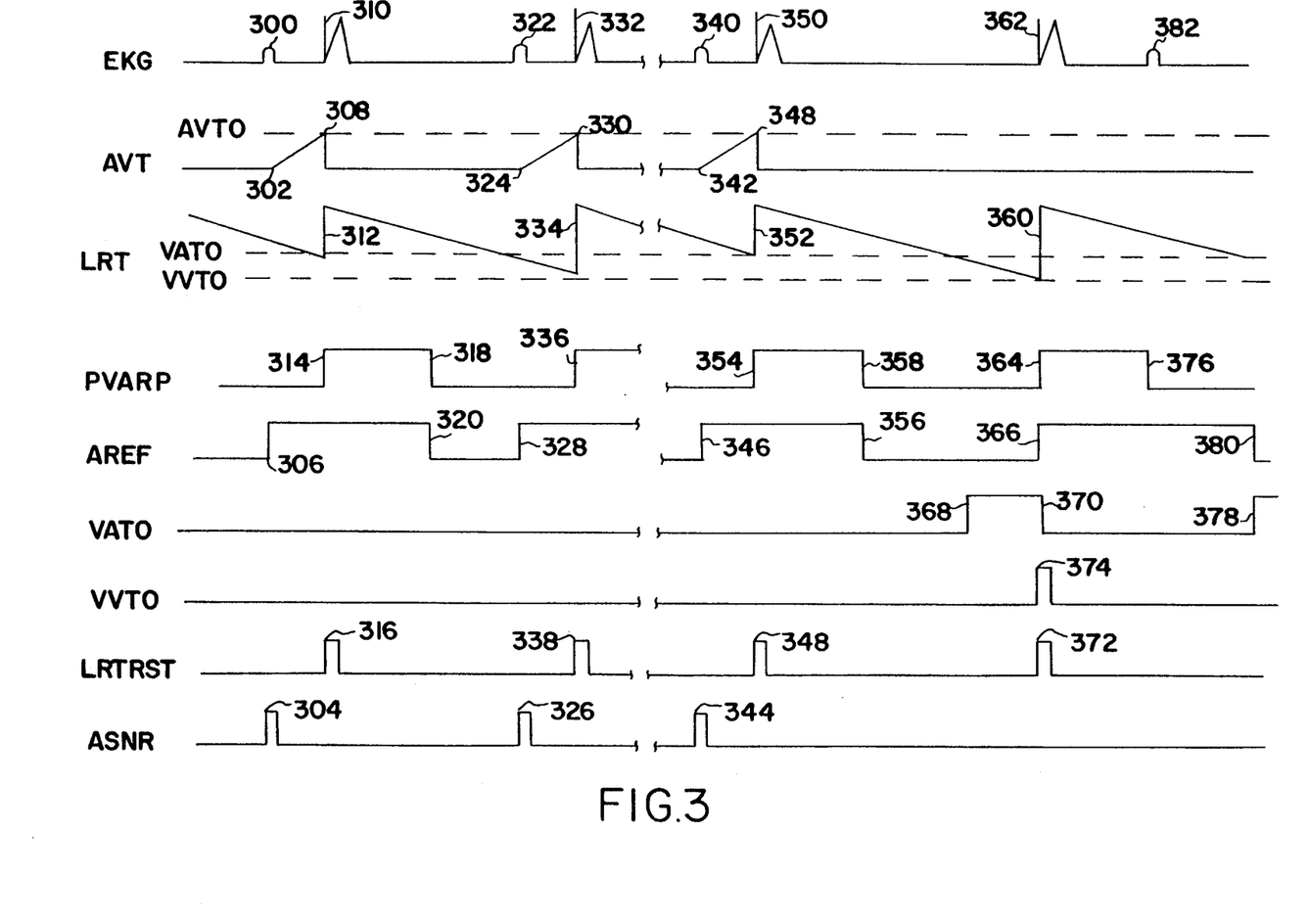
FIG. 3 illustrates the operation of the pacemaker illustrated in FIG. 1, with the present invention incorporated.

FIG. 2 illustrates the operation of a prior art DDD type pacemaker. The basic timing intervals illustrated are used in conjunction with a modified circuitry of FIG. 6 to provide the improved pacemaker of the present invention. FIG. 2 includes a simulated electrocardiogram (ECG) tracing at the top of the figure, with operation of the two main timers illustrated below. The two main timers include an A-V interval timer (AVT) which is illustrated as counting upward to a predetermined time-out value (AVTO), and a lower rate timer (LRT) which is illustrated as counting down to a predetermined V-A interval count (VATO) and a predetermined V-V interval count (VVTO). The A-V interval timer is initiated on sensing of natural atrial contractions. The lower rate timer is initiated on sensing of natural ventricular contractions or on delivery of a ventricular stimulation pulse. The A-V and lower rate timers are both contained within digital controller 18. The time period between VATO and VVTO may also be referred to as a second A-V interval, following atrial pacing pulses.

Digital controller 18 defines a postventricular atrial refractory period (PVARP), typically 400 ms. or less, and a ventricular upper rate interval (VURT) which are initiated on sensing of a natural ventricular contraction or on delivery of a ventricular pacing pulse. Digital controller 18 also provides logic signals including VATO, which is high from time-out of the V-A interval until delivery of a ventricular pacing pulse, VVTO which is high on time-out of the V-V interval and is reset on beginning of timing of the next subsequent V-V interval, LRT RST, indicative of reset of the lower rate timer, and ASNR, indicating sensing of an atrial contraction outside of the atrial refractory period as discussed below.

During a time interval beginning with sensing of a natural atrial contraction or time-out of the V-A interval, and extending until the expiration of the PVARP, signals from P-wave amplifier 10 will be ineffective to initiate timing of an A-V interval by digital controller 18. This period of time cumulatively is referred to as the atrial refractory period and its duration corresponds to a high logic signal AREF, as illustrated in FIGS. 2 and 3.

Time-out of the A-V interval during the ventricular upper rate interval will cause delivery of a ventricular pacing pulse at the end of the ventricular upper rate interval, as described in the above-cited Adams patent.

The ECG tracing in FIG. 2 begins with an atrial contraction 100, indicated by ASNR signal 102, which initiates timing of the A-V interval at 104, and begins the atrial refractory period (AREF) at 106. On time-out of the A-V interval at 108, digital controller 18 triggers ventricular output circuit 16 to deliver a ventricular pacing pulse 110. This also causes reset of the lower rate timer at 112, indicated by LRT RST signal 114. On reset of the lower rate timer, the postventricular atrial refractory period (PVARP) is also initiated at 116 and the VURT is initiated at 103. PVARP 116 extends until its time-out at 118, at which point the atrial refractory period (AREF) ends at 120. The VURT times out at 121. The lower rate timer continues to time until time-out of the V-A interval at 122, at which time digital controller 18 triggers atrial output circuit 14 to deliver an atrial pacing pulse 124. Because time-out of the V-A interval at 122 occurred prior to sensing of any natural atrial contractions, a high VATO signal is initiated at 126, which in turn reinitiates the atrial refractory period at 128. On time-out of the V-V interval at 130, indicated by provision of a positive VVTO signal at 132, digital controller 118 triggers ventricular output circuit 116 to deliver a ventricular pacing pulse 134. Concurrent with time-out of the V-V interval, the VATO signal is terminated at 136 and the lower rate timer is reset, indicated by a positive going LRT RST signal 134.

The simulated EKG in FIG. 2 continues, with the assumption that the atrial output has been disabled. That is, on time-out of the V-A interval (VATO) all other timing functions remain the same, but no atrial stimulating pulse is triggered. This is one fashion in which prior art DDD pacemakers could be programmed to exhibit a VDD type pacing mode. The simulated EKG continues with a sensed atrial contraction 140, and concurrent generation of a positive ASNR signal 142, initiation of the A-V interval at 144 and initiation of the atrial refractory period at 146. On time-out of the A-V interval at 148, a ventricular pacing pulse is triggered at 150, the postventricular atrial refractory period is initiated at 152, the ventricular upper rate interval is initiated at 143, the lower rate timer is reset at 154, and an LRT RST signal is generated at 150. On time-out of the PVARP at 158, the atrial refractory period terminates at 160. The VURT times out at 161. In the absence of sensed atrial contraction, the V-A interval times out at 162, initiating a positive VATO signal at 164. On timeout of the V-V interval at 166, a ventricular pacing pulse is triggered at 168, the PVARP is initiated at 170, the VURT is initiated at 177, the VATO signal is terminated at 172, and VVTO and LRT RST signals are generated at 174 and 176, respectively. On time-out of the PVARP at 178, the atrial refractory period ends at 180. Shortly thereafter, an atrial contraction occurs at 182. For purposes of this timing chart, it is assumed that the PVARP is set to a relatively short interval, such as 250 ms. As such, any atrial contraction occurring more than 250 ms from the immediately preceding ventricular pacing pulse will be sensed and effective to restart a new interval. As illustrated, it assumed that atrial pulse 182 is a result of atrial bradycardia. However, an atrial contraction could also be detected under this set of circumstances as a result of retrograde conduction. On sensing of the atrial contraction at 182, the A-V interval is initiated at 184, the atrial refractory period is restarted at 186, and a positive ASNR signal is generated at 188. On time-out of the A-V delay at 190, the upper rate interval has not expired. Therefore, generation of ventricular pacing pulse 192 is delayed until time-out of the upper rate interval at 200, at which time the lower rate timer is reset at 196, the PVARP is restarted at 194, and an LRT RST signal is generated at 198.

The circumstances discussed above are undesirable for two reasons. First, and most obviously, the ventricular pacing pulses 168 and 192 are separated by a relatively short interval (500 ms) in the absence of any apparent physiologic necessity for rapid ventricular pacing. Second, because the ventricular pacing pulse 192 is extended beyond the end of the A-V delay, the conduction system between the atrium and the ventricle may no longer be refractory, and may conduct upward to the atrium, inducing an atrial contraction, typically between 200 and 400 ms thereafter. If this retrograde atrial contraction occurs after the end of the postventricular atrial refractory period, it will in turn initiate timing of a subsequent A-V interval, and generation of a ventricular pacing pulse at the expiration of the upper rate time interval. This behavior, when it persists, is known as pacemaker-mediated tachycardia.

As discussed above, pacemakers according to the prior art generally attempted to deal with the problem of pacemaker-mediated tachycardia by providing lengthened postventricular atrial refractory periods, either at all times, or as a result of complicated sensing algorithms which attempted to identify the occurrence of pacemaker-mediated tachycardia, and lengthen the PVARP in response. A pacemaker according to the present invention, on the other hand, does not attempt to detect the occurrence of retrograde conduction and/or initiation of pacemaker-mediated tachycardia, but instead attempts to prevent retrograde conduction or bradycardic atrial contractions from inappropriately initiating timing of the A-V interval. Functioning of a pacemaker according to the present invention is illustrated in FIG. 3, with the circuit modification required to transform a prior art DDD type pacemaker into a pacemaker according to the present invention illustrated in FIG. 5. Operation of the circuitry in FIG. 5 can best be understood by reviewing its operation in conjunction with the timing diagrams illustrated in FIGS. 3 and 4.

Figure 4:
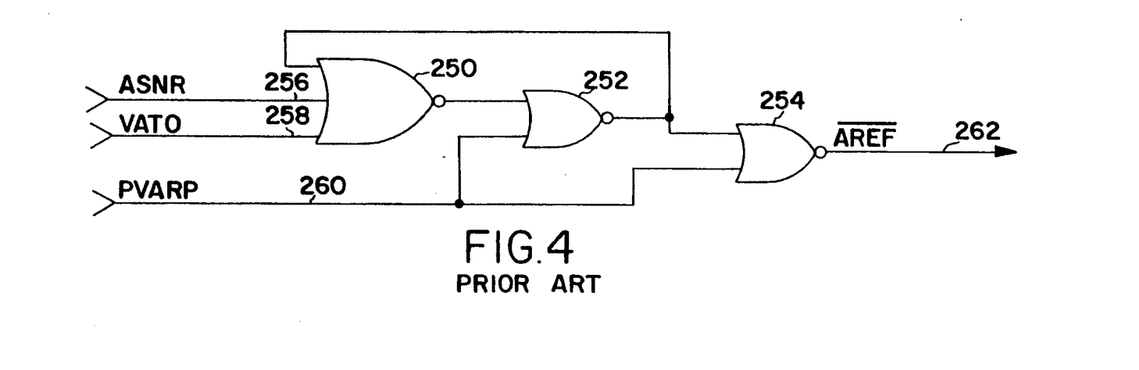
FIG. 4 illustrates a portion of the circuitry within a prior art pacemaker of the general type illustrated in FIG. 1. This circuitry determines the atrial refractory period of the pacemaker.

FIG. 4 is an example of circuitry for defining the atrial refractory period in a pacemaker as described in conjunction with FIGS. 1 and 2 above. In this prior art circuitry, the atrial refractory period, indicated by a low signal on AREF line 262 extends from a positive going transition on ASNR line 256 or VATO line 258 until the expiration of the postventricular atrial refractory period, indicated by a negative-going transition on PVARP line 260. NORgates 250 and 252 function as a set-reset flip-flop, set by positive-going transitions on ASNR line 256 or VATO line 258, driving the output of NORgate 254 low, indicating that the atrial refractory period is in effect. On a positive-going signal on PVARP line 260, the set/reset flip-flop is reset, driving the output of NORgate 252 low. However, as the PVARP line 260 is now high, the output of gate 254 on AREF line 262 remains low. On expiration of the postventricular atrial refractory period, PVARP line 260 goes low, allowing the output of gate 254 to go high, signaling the end of the atrial refractory period.

In order to practice an invention according to the present invention, some modifications to the prior art circuitry are required. In the same respect that the prior art circuitry illustrated in FIG. 4 is merely intended as an example, the circuit illustrated in FIG. 5 is similarly intended as an example of the sort of implementation which will provide the benefits of the present invention.

Figure 5:
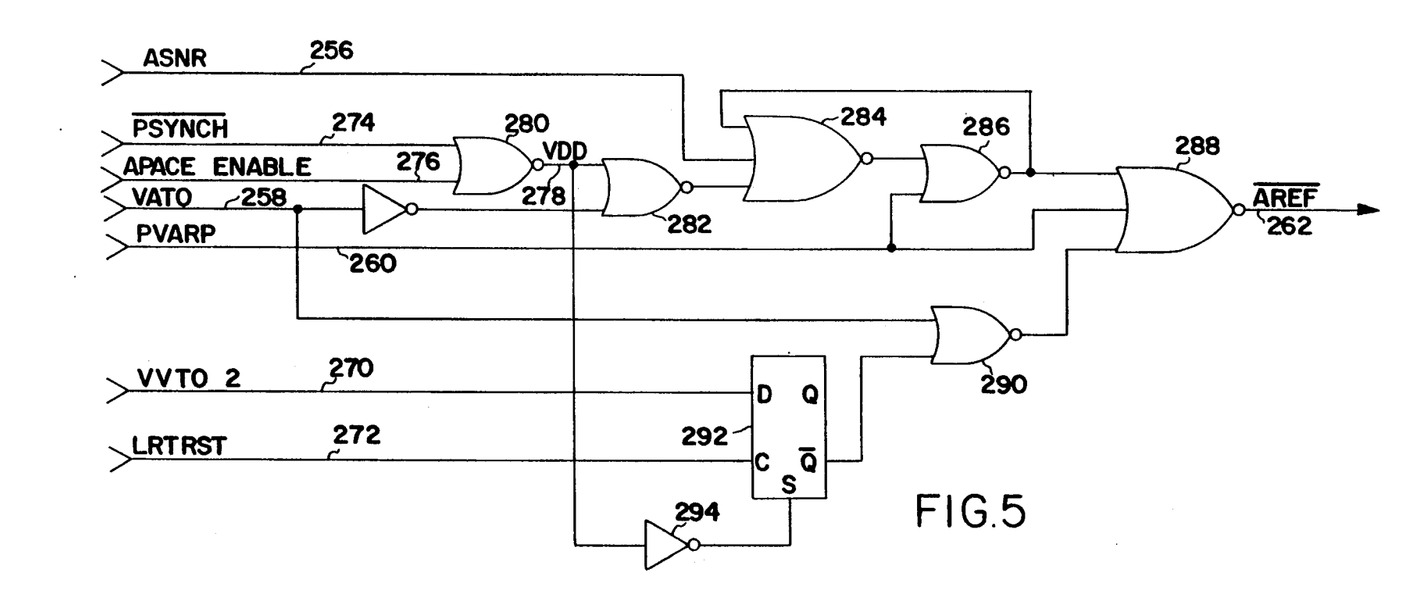
FIG. 5 shows modified circuitry according to the present invention, for defining the refractory periods in a pacemaker according to the present invention.

In addition to the ASNR line 256, VATO line 258 and PVARP line 260, the circuitry of FIG. 5 includes several other input signal lines. VVTO line 270 and LRT RST line 272 carry the identically named logic signals illustrated in FIGS. 2 and 3. In addition, PSYNCH line 274 and APACE ENABLE line 276 are provided, carrying signals from the memory within the digital controller 18, indicative of the fact that the pacemaker has been programmed to disable atrial pacing (APACE ENABLE line 276 is low) and that a P-synchronous pacing mode (DDD) has been selected (low signal on PSYNCH line 274). This produces a high output signal on VDD line 278, which indicates that the pacemaker has been programmed to behave as a VDD pacemaker and also activates the dual atrial refractory periods provided by the present invention.

NORgates 284 and 286 correspond to NORgates 250 and 252 illustrated in FIG. 4, and comprise a set/reset flip-flop. Operation of the circuit differs in that time-out of the V-A interval, indicated by a high signal on VATO line 258 is only allowed through to reset the set/reset flip-flop comprising NORgates 284 and 286 in the presence of a low signal on VDD line 278, indicating that VDD pacing mode has not been selected. In this circumstance, the circuitry of FIG. 5 functions identically to that of the circuitry of FIG. 4. However, if VDD line 278 is high, time-out of the V-A interval is ineffective to initiate the atrial refractory period, being blocked at NORgate 282. As such, the set/reset flip-flop comprising NORgates 284 and 286 will only be reset by a positive-going transition on ASNR line 256. The high signal on PVARP line 260 indicative of the timing of the postventricular atrial refractory period functions identically to that illustrated in FIG. 4. On a positive-going transition on PVARP line 260, the set/reset flip-flop comprising NORgates 284 and 286 is reset. A high signal on line 260 ensures a low signal on AREF line 262 indicating the duration of the atrial refractory period. The low signal on AREF line 262 thus persists from sensing of an atrial contraction indicated by a high signal on ASNR line 256 until termination of the postventricular atrial refractory period indicated by a negative-going transition on line 260.

However, in the event that a ventricular pacing pulse is generated due to time-out of the lower rate timer, a second, longer postventricular atrial refractory period is selected, and the atrial refractory period begins in this case with delivery of the ventricular pacing pulse. In this case, the longer atrial refractory period corresponds to the inverse of the signal on VATO line 258. In the event that the lower rate timer is reset, indicated by a positive pulse on LRT RST line 272, and the V-V interval has not timed out, the low signal on VVTO line 270 will be clocked through D-type flip-flop 292, producing a high signal on the Q output of flip-flop 292, which sets the output of NORgate 290 low, preventing the logic state on VATO line 258 from affecting the atrial refractory period defined on line 262. However, if the lower rate timer is reset as a result of time-out of the V-V or lower rate interval, the positive signal on VVTO line 270 will be clocked through flip-flop 294, setting the Q output of flip-flop 292 low. In this case, while VATO line 258 is low, the output of NORgate 290 will be high, setting the output of NORgate 288 low. Thus, following a ventricular pacing pulse generated due to time-out of the V-V interval defined by the lower rate timer, an atrial refractory period is defined which extends for the duration of the V-A interval.

In order for the present invention to work optimally, it is preferred that the pacemaker be programmable to define different A-V intervals following atrial pacing pulses or sensed atrial contractions. Preferably, the V-A interval defined by the pacemaker should be less than the V-V interval minus the time interval defined by the A-V timer. This will provide an opportunity for the pacemaker to resynchronize to natural atrial contractions occurring at a rate greater than that provided by the lower rate timer. For example, appropriate settings for the various intervals timed might include a V-V or lower rate interval of 800 ms, a V-A interval defined by the lower rate timer of 550 ms, an A-V interval defined by the A-V timer of 150 ms, and a 250 ms PVARP interval. These settings are used in conjunction with the simulated ECG and associated timing charts illustrated in FIG. 3.

In FIG. 3, the simulated ECG begins with a sensed atrial contraction 300, which initiates timing of the 150 ms A-V interval at 302 and also causes generation of a positive ASNR signal at 304. As illustrated in conjunction with FIG. 5, this initiates the atrial refractory period at 306. On time-out of the A-V interval at 308, a ventricular pacing pulse is generated at 310, the lower rate timer is reset at 312, the postventricular atrial refractory period is initiated at 314, and a positive LRT RST signal is generated at 316. Because the V-V interval had not timed out when LRT RST signal 316 was generated, the PVARP signal will define the remainder of the duration of the atrial refractory period. On time-out of the PVARP at 318, the atrial refractory period ends at 320, allowing sensing of a subsequent atrial contraction at 322. As such, the pacemaker is capable of following naturally occurring high atrial rates up to a rate equal to either the rate defined by a ventricular upper rate timer discussed above, or to a rate corresponding to the interval defined by the sum of the A-V interval defined by the A-V timer plus the postventricular atrial refractory period. In the case of FIG. 3, with the intervals defined as listed above, the pacemaker is able to track naturally-occurring atrial rates up to 150 beats per minute (AV+PVARP=400 ms).

On sensing of an atrial contraction at 322, the A-V interval is initiated at 324, an ASNR signal is generated at 326, reinitiating the atrial refractory period at 328. On time-out of the A-V interval at 330, a ventricular pacing pulse 332 is generated, the lower rate timer is reset at 334, and the postventricular atrial refractory period is initiated at 336. Because LRT RST signal 338 occurs prior to time-out of the V-V interval, the effective refractory period will again extend until the termination of the PVARP.

The second half of the diagram illustrates the situation in which ventricular pacing pulses are generated in response to time-out of the V-V interval, by the lower rate timer. Again, an atrial contraction at 340 starts the timing of the A-V interval at 342 and triggers generation of an ASNR signal at 344, which in turn initiates the atrial refractory period at 346. On time-out of the A-V interval at 348, a ventricular pacing pulse 350 is generated, the lower rate timer is reset at 352, the PVARP is initiated at 354 and an LRT RST signal is generated at 348. Again, as the LRT RST signal occurred prior to time-out of the V-V interval, the effective atrial refractory period terminates at 356, concurrent with termination of the PVARP at 358.

In the absence of natural atrial activity, the V-V interval times out at 360, triggering generation of ventricular pacing pulse 362 and initiating time-out of the PVARP at 364. Because there was no natural atrial contraction prior to ventricular pacing pulse 362, initiation of the atrial refractory period is delayed until delivery of the ventricular pacing pulse, at 366. Because the pacemaker is programmed into VDD mode, the positive going VATO signal at 368 is not effective to start the atrial refractory period. On delivery of the ventricular pacing pulse, the VATO signal is terminated at 370, and an LRT RST signal is generated at 372. Because the V-V interval timed out is indicated by a positive signal at 374, the atrial refractory period is extended past the expiration of the PVARP at 376 and extends until the next positive going transition at 378 indicative of time-out of a V-A interval. At this point, the atrial refractory period terminates at 380.

Unlike the corresponding rhythm strip illustrated in FIG. 2, an atrial contraction 382 occurring shortly after the expiration of the PVARP period following ventricular pacing pulse 362 is not effective to initiate timing of an A-V interval, as it occurs within the lengthened postventricular atrial refractory period defined by the duration of the V-A interval. Because the V-A interval extends for only 550 ms following A-V ventricular pacing pulse 362, this effectively provides a time interval of 100 ms following V-A interval time-out at 380 during which an atrial contraction would be effective to initiate timing of the A-V delay interval determined by the A-V delay timer. This allows the pacemaker to resynchronize to natural atrial rates. After such a natural atrial contraction, the refractory period following the next ventricular pacing pulse would extend for the fixed PVARP period, rather than for the V-A interval determined by the lower rate counter.

In the specific embodiment disclosed above as illustrated in FIGS. 1 and 2, sensing of an atrial contraction at a time that precedes time out of the V-V interval (VVTO) by less than the duration of the A-V delay determined by the A-V delay timer will not result in the generation of a ventricular synchronized pacing pulse. Instead, the ventricular pacing pulse will be delivered on time out of the V-V interval. However, it is also contemplated that the present invention may be practiced in the context of a pacemaker in which time out of the V-V interval (VVTO) is disabled from triggering a ventricular pacing pulse, during timing of the A-V delay determined by the A-V delay timer. In such a device, in the circumstances discussed above, a 250 ms. synchronization window would be provided, during which sensing of an atrial contraction would serve to trigger generation of a synchronous ventricular pacing pulse. The operation of such a device is illustrated in FIG. 6.

Figure 6:
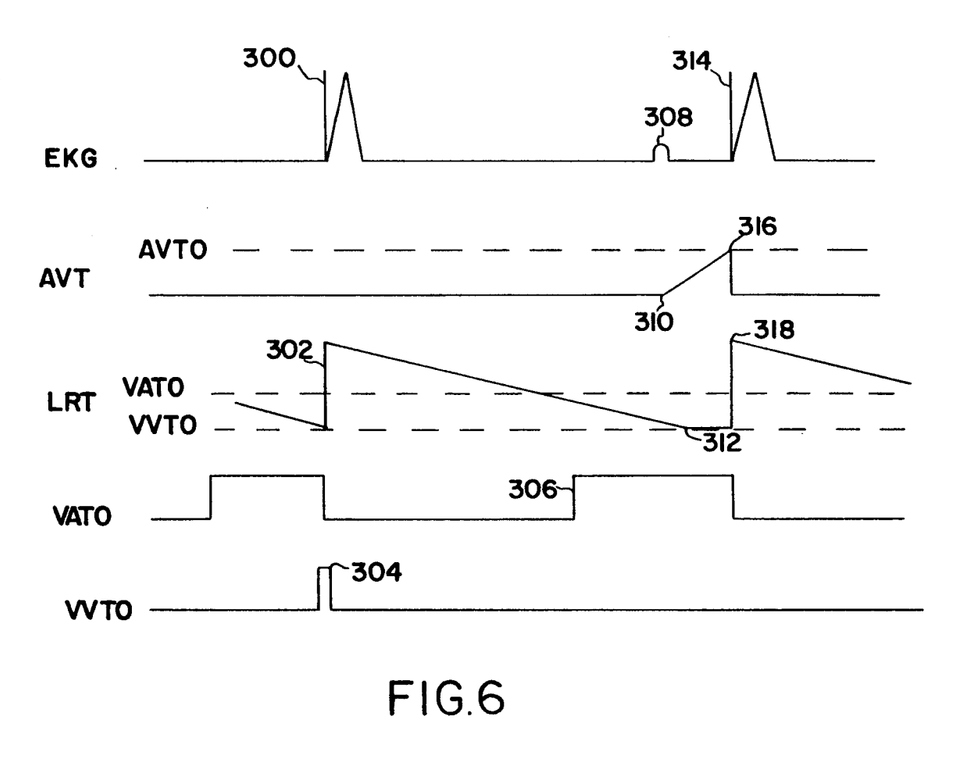
FIG. 6 illustrates the operation of an alternate embodiment of a pacemaker with the present invention incorporated.

FIG. 6 shows the operation of the above discussed alternate embodiment of the device, assuming that all programmed parameters are set equal to those described in 5 conjunction with FIG. 3. The simulated EKG strip begins with a ventricular pacing pulse 300, generated on time out of the V-V interval at 302. A VVTO signal is generated at 304, which serves to select the V-A interval as the effective refractory period. After the expiration of the V-A interval at 306, atrial sensing is enabled. At 308, a natural atrial contraction is sensed, initiating timing of the A-V interval at 310. In the embodiment illustrated in FIG. 6, it is contemplated that the VVTO signal will be disabled from triggering a ventricular pacing pulse during the timing of the A-V interval defined by the A-V delay timer. Therefore, on expiration of the V-V interval at 312, a ventricular pacing pulse is not triggered. Instead, the A-V delay timer is allowed to continue timing its A-V interval, triggering generation of a pacing pulse at 314, on the expiration of the A-V interval at 316. Because no VVTO signal is not present on reset of the lower rate timer at 318, the effective atrial refractory period will be the programmed atrial refractory period, rather than the V-A interval. A pacemaker according to the embodiment illustrated in FIG. 6 is believed particularly desirable in the context of a rate responsive pacemaker, as it allows the pacemaker to follow the natural atrial rate, even if it is slightly lower than the sensor indicated pacing rate.

As described in the above cited Markowitz patent, pacemakers are now available which vary the effective duration of the V-A interval as a function of the output of a physiologic sensor of the demand for cardiac output. Similarly, as described in the above cited Funke et al patent, it is known to provide a V-A interval which varies as a function of the measured natural atrial rate. The present invention is believed easily practiced in either type of pacemaker. Because the variable refractory period provided by the present invention following time-out of the V-V interval extends from the beginning of the V-V interval until expiration of the V-A interval, variation in the V-A or V-V interval will automatically produce a variation in the effective postventricular atrial refractory period such that with a decrease in the V-A interval, a corresponding decrease in the postventricular atrial refractory period occurs. This provides a simple and elegant method of providing a rate variable postventricular atrial refractory period for either a pacemaker as described in the Funke patent or a pacemaker as described in the Markowitz et al patent. For purposes of the present invention, the timing chart of FIG. 3 is equally applicable to such pacemakers, with only the added understanding that the duration of the V-A interval varies as a function of a measured parameter such as atrial rate or physical activity. Again, when the invention is practiced in devices as generally disclosed in the above cited Funke and Markowitz et al patents, it is desirable that the A-V interval defined following a sensed atrial contraction be adjustable to a lesser value than the A-V interval normally following generation of an atrial pacing pulse due to time-out of the V-A interval. As discussed in conjunction with FIGS. 3 and 5, this will provide for resynchronization to atrial rates occurring at a rate slightly more rapid than the rate at which ventricular pacing pulses would normally be generated by the pacemaker.

While the invention is illustrated in the present application may be practiced by a circuitry modification to a prior art DDD or DDDR type pacemaker, it can be practiced in the context of a wide variety of pacemakers, providing that the pacemaker has the capability to sense atrial contractions, to define at least the following characteristics. The pacemaker should be able to sense in the atrium and define an A-V delay after sensing in the atrium at the expiration of which ventricular pacing pulse is triggered. The pacemaker should define an interval between successive ventricular pacing pulses in the absence of natural atrial and ventricular contractions. While in the present application this takes the form of a V-V interval initiated on ventricular pacing and sensing, it is possible that the lower rate interval might also be defined by timer intervals as extending from atrial events to subsequent atrial events. The pacemaker should also include a timer which defines an interval following a ventricular pacing pulse, and extending to a predetermined time prior to the delivery of the next subsequent ventricular pacing pulse in the absence of natural atrial and ventricular contractions. In the context of the invention as illustrated above, this takes the form of the V-A interval which would normally be used for triggering atrial pacing pulses, if the pacemaker were to be used in DDD or DDDR mode. However, it is within the scope of the invention to employ the invention in a pacemaker which is dedicated to VDD pacing, in which case the interval corresponding to the V-A interval illustrated in the present case would not normally be used for triggering atrial pacing pulses. The pacemaker should also define an atrial refractory period extending from ventricular pacing pulses, for a predetermined period thereafter, which is generally shorter than the interval corresponding to the V-A interval, to provide for an effectively shorter atrial refractory period in the presence of high natural atrial rates. The present invention is believed to be readily practiced in the context of any pacemaker employing at least these functional characteristics. As such, the embodiments discussed above should be considered exemplary, rather than limiting with regard to the following claims.

In conjunction with the above specification, I claim:

1. In a pacemaker, comprising:
   atrial sensing means for sensing natural atrial contractions;
   atrial pulse generator means for generating atrial pacing pulses;
   ventricular sensing means for sensing natural ventricular contractions;
   ventricular pulse generator means for generating ventricular pacing pulses;
   timing means for defining V-A intervals following generation of ventricular pacing pulses by said ventricular pulse generator means and for triggering said atrial pulse generator means to generate atrial pacing pulses at the expiration of said V-A intervals, for defining first A-V intervals initiated on sensing of natural atrial contractions by said atrial sensing means and for triggering said ventricular pulse generator means to generate ventricular pacing pulses at the expiration of said first A-V intervals, for defining second A-V intervals following said V-A intervals and for triggering said ventricular pulse generator means to generate ventricular pacing pulses at the expiration of said second A-V intervals, and for defining post-ventricular atrial refractory periods following generation of ventricular pacing pulses by said ventricular pulse generator means, during which periods natural atrial contractions sensed by said atrial sensing means are ineffective to initiate timing of said first A-V intervals;

the improvement comprising:

means for operating said pacemaker in VDD pacing mode comprising means for preventing expiration of said V-A intervals from triggering said atrial pulse generator means to generate atrial pacing pulses, means for defining first postventricular atrial refractory periods of 400 milliseconds or less following ventricular pacing pulses triggered on expiration of said first A-V intervals and for defining post ventricular atrial refractory periods equal to said V-A intervals following generation of ventricular pacing pulses at the expiration of said second A-V intervals.

2. A pacemaker according to claim 1 wherein said second A-V intervals are longer than said first A-V intervals.

3. A pacemaker according to claim 1 or claim 2 further comprising a sensor means for sensing physiologic demand for cardiac output and means responsive to said sensor means for modifying the duration of said V-A intervals determined by said timing means as a function of said physiologic demand for cardiac output.

4. A pacemaker according to claim 1 wherein said means for selecting selects a post ventricular atrial refractory period of about 250 ms. following generation of ventricular pacing pulses at the expiration of said first A-V intervals.

5. A pacemaker according to claim 1 wherein said second A-V intervals are at least about 100 ms. greater in duration than said first A-V intervals.

6. A pacemaker according to claim 4 or claim 5 wherein said pacemaker further comprises sensor means for sensing the physiologic demand for oxygenated blood and means responsive to said sensor means for varying the duration of said V-A intervals determined by said timing means as a function of said physiologic demand for oxygenated blood.

* * * * *